(12) United States Patent
Protat-Gerardin et al.

(10) Patent No.: US 12,016,946 B2
(45) Date of Patent: Jun. 25, 2024

(54) PROCESS FOR THE TREATMENT OF KERATIN FIBERS EMPLOYING A COMPOSITION COMPRISING AT LEAST ONE ALKOXYSILANE OF FORMULA (I), AT LEAST ONE NON AMINO SILICONE OF FORMULA (II) HAVING A WEIGHT-AVERAGE MOLECULAR WEIGHT OF LESS THAN OR EQUAL TO 1500 G/MOL AND AT LEAST ONE COLORING AGENT

(71) Applicant: L'OREAL, Paris (FR)

(72) Inventors: Marine Protat-Gerardin, Saint-Ouen (FR); Alexis Liard, Saint-Ouen (FR); Jean-Daniel Debain, Saint-Ouen (FR)

(73) Assignee: L'OREAL, Paris (FR)

( * ) Notice: Subject to any disclaimer, the term of this patent is extended or adjusted under 35 U.S.C. 154(b) by 73 days.

(21) Appl. No.: 17/919,694

(22) PCT Filed: Apr. 20, 2021

(86) PCT No.: PCT/EP2021/060239
§ 371 (c)(1),
(2) Date: Oct. 18, 2022

(87) PCT Pub. No.: WO2021/214056
PCT Pub. Date: Oct. 28, 2021

(65) Prior Publication Data
US 2023/0201102 A1 Jun. 29, 2023

(30) Foreign Application Priority Data
Apr. 24, 2020 (FR) .................................... 2004112

(51) Int. Cl.
*A61Q 5/10* (2006.01)
*A61K 8/891* (2006.01)
*A61Q 5/06* (2006.01)

(52) U.S. Cl.
CPC .............. *A61K 8/891* (2013.01); *A61Q 5/065* (2013.01); *A61K 2800/432* (2013.01)

(58) Field of Classification Search
CPC .. A61K 8/891; A61K 2800/432; A61K 8/585; A61K 8/892; A61Q 5/065; A61Q 5/10
USPC .......................................................... 8/405
See application file for complete search history.

(56) References Cited

U.S. PATENT DOCUMENTS

| 4,578,266 A | 3/1986 | Tietjen et al. |
| 5,645,609 A | 7/1997 | Andrean et al. |
| 5,708,151 A | 1/1998 | Möckli |
| 2010/0083446 A1* | 4/2010 | Brun ...................... A61K 8/891 8/405 |
| 2013/0209921 A1 | 8/2013 | Qiu et al. |
| 2018/0369123 A1* | 12/2018 | Lion ........................ A61K 8/41 |
| 2020/0101004 A1* | 4/2020 | Chodorowski-Kimmes ................ A61K 8/41 |

FOREIGN PATENT DOCUMENTS

| EP | 0714954 A2 | 6/1996 |
| EP | 1184426 A2 | 3/2002 |
| FR | 2679771 A1 | 2/1993 |
| FR | 2936414 A1 | 4/2010 |
| JP | 05-017710 A | 1/1993 |
| JP | 07-258460 A | 10/1995 |
| JP | 09-188830 A | 7/1997 |
| JP | 10-158450 A | 6/1998 |
| JP | 10-158451 A | 6/1998 |
| WO | 95/01772 A1 | 1/1995 |
| WO | 95/15144 A1 | 6/1995 |
| WO | 2017/102857 A1 | 6/2017 |
| WO | WO 2017102857 A1 * | 6/2017 ............... A61Q 5/06 |

OTHER PUBLICATIONS

STIC Search Report dated Feb. 6, 2024.*
International Search Report and Written Opinion for counterpart Application No. PCT/EP2021/060239, dated Jul. 16, 2021.
Schlossman, Mitchell L., "Treated Pigments New Ways to Impart Color on the Skin," Cosmetics and Toiletries, vol. 105, Feb. 1990, pp. 53-64.

* cited by examiner

Primary Examiner — Eisa B Elhilo
(74) Attorney, Agent, or Firm — THE MARBURY LAW GROUP, PLLC

(57) ABSTRACT

A subject matter of the present invention is a process for the treatment of keratin fibers, such as the hair, comprising the application, to the keratin fibers, of a composition comprising at least one alkoxysilane chosen from the compounds of formula (I), at least one non amino silicone of formula (II), the non amino silicone(s) of formula (II) having a weight-average molecular weight of less than or equal to 1500 g/mol and at least one coloring agent chosen from pigments, direct dyes and their mixtures, followed by a stage of application of heat to the keratin fibers covered with the composition, using a heating tool, at a temperature of greater than or equal to 45° C. for a period of time of greater than or equal to 15 minutes.

20 Claims, No Drawings

PROCESS FOR THE TREATMENT OF KERATIN FIBERS EMPLOYING A COMPOSITION COMPRISING AT LEAST ONE ALKOXYSILANE OF FORMULA (I), AT LEAST ONE NON AMINO SILICONE OF FORMULA (II) HAVING A WEIGHT-AVERAGE MOLECULAR WEIGHT OF LESS THAN OR EQUAL TO 1500 G/MOL AND AT LEAST ONE COLORING AGENT

CROSS REFERENCE TO RELATED APPLICATIONS

This is a National Stage Application of PCT/EP2021/060239, filed internationally on Apr. 20, 2021, which claims priority to French Application No. 2004112, filed on Apr. 24, 2020, the contents of both of which are incorporated by reference herein in their entireties.

A subject matter of the present invention is a process for the treatment of keratin fibers, such as the hair, comprising the application, to the keratin fibers, of a composition comprising at least one alkoxysilane chosen from the compounds of formula (I), at least one non amino silicone of formula (II), the non amino silicone(s) of formula (II) having a weight-average molecular weight of less than or equal to 1500 g/mol and at least one coloring agent chosen from pigments, direct dyes and their mixtures, followed by a stage of application of heat to the keratin fibers covered with the composition, using a heating tool, at a temperature of greater than or equal to 45° C. for a period of time of greater than or equal to 15 minutes.

Another subject matter of the present invention is a method for the treatment of keratin fibers, such as the hair, employing a mixture of two compositions (A) and (B).

TECHNICAL FIELD

In the field of the dyeing of keratin fibers, in particular human keratin fibers, it is already known practice to dye keratin fibers via various techniques starting from direct dyes or pigments for nonpermanent dyeing or from dye precursors for permanent dyeing.

There are essentially three types of process for dyeing the hair:
a) "permanent" dyeing, the function of which is to afford a substantial modification to the natural color and which employs oxidation dyes which penetrate into the hair fiber and forms the dye via an oxidative condensation process;
b) nonpermanent, semipermanent or direct dyeing, which does not employ the oxidative condensation process and withstands four or five shampooing operations; it consists in dyeing keratin fibers with dye compositions containing direct dyes;
c) temporary dyeing, which gives rise to a modification to the natural color of the head of hair which remains from one shampooing operation to the next, and which serves to enhance or correct a shade which has already been obtained. It can also be likened to a "makeup" process.

For this last type of dyeing, it is known practice to use colored polymers formed by grafting one or more dyes of azo, triphenylmethane, azine, indoamine or anthraquinone nature to a polymer chain. These colored polymers are not entirely satisfactory, in particular as regards the homogeneity of the coloring obtained and its resistance, not to mention the problems associated with their manufacture and in particular with their reproducibility.

Another dyeing method consists in using pigments. Specifically, the use of pigment at the surface of keratin fibers generally makes it possible to obtain visible colorings on dark hair, since the surface pigment masks the natural color of the fiber. However, the colorings obtained via this dyeing method exhibit the disadvantage of having poor resistance to shampooing operations and also to external agents, such as sebum, perspiration, brushing and/or rubbing actions.

The need thus remains to have available a process for the treatment of keratin fibers, in particular the hair, which exhibits the advantage of obtaining a homogeneous and smooth colored sheathing on the hairs, while forming a coating which is persistent toward shampooing operations and to the various attacking factors to which the hair may be subjected, such as brushing and/or rubbing actions, without degrading the hair.

Thus, the aim of the present invention is to develop a process for the treatment of keratin fibers, in particular the hair, which exhibits the advantage of obtaining a homogeneous and smooth colored sheathing on the hairs, while forming a coating which is persistent toward shampooing operations and to the various attacking factors to which the hair may be subjected, such as brushing and/or rubbing actions, without degrading the hair.

Account of the Invention

The present invention relates to a process for the treatment of keratin fibers, such as the hair, comprising the application, to the keratin fibers, of a composition comprising;
a) at least one alkoxysilane chosen from the compounds of formula (I) as described below, their oligomers and/or their mixtures;
b) at least one non amino silicone of formula (II) as described below, the non amino silicone(s) of formula (II) having a weight-average molecular weight of less than or equal to 1500 g/mol; and
c) at least one coloring agent chosen from pigments, direct dyes and their mixtures, followed by a stage of application of heat to the keratin fibers covered with the composition, using a heating tool, at a temperature of greater than or equal to 45° C. for a period of time of greater than or equal to 15 minutes.

The present invention also relates to a process for the treatment of keratin fibers, such as the hair, which consists in extemporaneously mixing, at the time of use, two compositions (A) and (B) and in applying the mixture to the fibers, with:
the composition (A) comprising at least one alkoxysilane chosen from the compounds of formula (I) as described below, their oligomers and/or their mixtures;
the composition (B) comprising at least one non amino silicone of formula (II) as described below;
it being understood that the composition (A) and/or the composition (B) comprise at least one coloring agent chosen from pigments, direct dyes and their mixtures, followed by a stage of application of heat to the keratin fibers covered with the composition, using a heating tool, at a temperature of greater than or equal to 45° C. for a period of time of greater than or equal to 15 minutes.

By the use of this process for the treatment of keratin fibers, colored sheathings are obtained on the hairs which make it possible to obtain a coloring which is visible on all types of hair in a manner which is persistent toward shampooing operations, while preserving the physical qualities of the keratin fibers. Such a sheathing may be resistant to the external attacking factors to which the hair may be subjected, such as blow drying and perspiration. It makes it possible in particular to obtain a smooth and uniform deposit.

Within the meaning of the present invention, "alkoxysilane" is understood to mean an alkoxysilane or an alkoxysilane oligomer of formula (I).

Within the meaning of the present invention, "coloring which is persistent with regard to shampooing operations" is understood to mean that the coloring obtained persists after one shampooing operation, preferably after three shampooing operations, more preferentially after five shampooing operations.

The expression "at least one" means one or more.

The invention is not limited to the examples illustrated. The characteristics of the various examples can in particular be combined within alternative forms which are not illustrated.

Within the meaning of the present invention and unless otherwise indicated,
- an "alkyl" radical denotes a saturated and linear or branched radical containing, for example, from 1 to 20 carbon atoms;
- an "aminoalkyl" radical denotes an alkyl radical as defined above, said alkyl radical comprising an $NH_2$ group;
- a "cycloalkyl" radical denotes a saturated cyclic hydrocarbon group comprising from 1 to 3 rings, preferably 2 rings, and comprising from 3 to 20 carbon atoms, preferably between 5 and 10 carbon atoms, such as cyclopentyl, cyclohexyl, cycloheptyl, norbornyl or isobornyl, it being possible for the cycloalkyl radical to be substituted by one or more $(C_1-C_4)$alkyl groups, such as methyl,
- an "aryl" radical is an aromatic unsaturated cyclic radical comprising from 6 to 12 carbon atoms which is mono- or bicyclic and fused or nonfused; preferably, the aryl group comprises 1 ring having 6 carbon atoms, such as phenyl;
- an "alkoxy" radical denotes an alkyl-oxy radical with "alkyl" as defined above.

The process for the treatment of keratin fibers according to the invention is preferably a process for dyeing keratin fibers, such as the hair.

"Keratin fibers" is understood particularly to mean human keratin fibers, such as the hair, eyelashes, eyebrows and body hair, preferentially the hair, eyebrows and eyelashes, more preferentially still the hair.

Alkoxysilane of Formula (I):

The process according to the invention comprises a composition comprising at least one alkoxysilane chosen from the compounds of following formula (I), their oligomers and/or their mixtures:

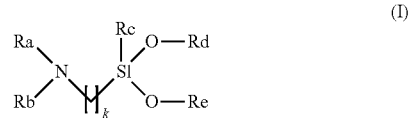

(I)

in which:
Ra and Rb, which are identical or different, represent a hydrogen atom; an alkyl group having from 1 to 20 carbon atoms, preferably from 1 to 10 carbon atoms and in particular from 1 to 4 carbon atoms; a cycloalkyl group having from 3 to 20 carbon atoms, preferably 5 or 6 carbon atoms; an aryl group having from 6 to 12 carbon atoms; an aminoalkyl group having from 1 to 20 carbon atoms;

Rc represents a hydrogen atom; an alkyl group having from 1 to 20 carbon atoms, preferably from 1 to 10 carbon atoms, more preferentially from 1 to 4 carbon atoms and in particular from 1 to 2 carbon atoms, such as a methyl; an alkoxy group having from 1 to 10 carbon atoms, preferably from 1 to 4 carbon atoms and in particular from 1 to 2 carbon atoms, such as an ethoxy;

Rd and Re, which are identical or different, represent an alkyl group having from 1 to 10 carbon atoms, preferably from 1 to 4 carbon atoms, in particular from 1 to 2 carbon atoms, such as an ethyl;

k denotes an integer ranging from 0 to 5, in particular from 1 to 3.

"Oligomer" is understood to mean the compound(s) comprising at least two silicon atoms which are obtained by oligomerization or polymerization of the compounds of formula (I).

Preferably, the alkoxysilane(s) of formula (I) are such that:
Ra and Rb, which are identical, represent a hydrogen atom; or Ra denotes a hydrogen atom and Rb denotes a cycloalkyl group having from 3 to 20 carbon atoms, in particular 5 or 6 carbon atoms;

Rc represents an alkyl group having from 1 to 10 carbon atoms, in particular from 1 to 4 carbon atoms and especially from 1 to 2 carbon atoms, preferably a methyl, or an alkoxy group having from 1 to 4 carbon atoms, preferably from 1 to 2 carbon atoms, preferably an ethoxy;

Rd and Re, which are identical or different, represent an alkyl group having from 1 to 10 carbon atoms, preferably from 1 to 4 carbon atoms, such as an ethyl;

k denotes an integer ranging from 1 to 3 and more particularly 1 or 3.

More preferentially, the alkoxysilane(s) of formula (I) are such that:
Ra and Rb, which are identical, represent a hydrogen atom;

Rc represents an alkoxy group having from 1 to 4 carbon atoms, preferably from 1 to 2 carbon atoms, preferably an ethoxy;

Rd and Re, which are identical or different, represent an alkyl group having from 1 to 4 carbon atoms, preferably an ethyl;

k denotes an integer equal to 1 or 3, preferably equal to 3.

More preferentially still, the alkoxysilane(s) of formula (I) are such that Ra and Rb represent a hydrogen atom, Rc represents an ethoxy group, Rd and Re are identical and represent an ethyl and k is equal to 3.

Mention may in particular be made, among the alkoxysilanes of formula (I), their oligomers and/or their mixtures, of 3-aminopropyltriethoxysilane (APTES), 3-aminopropylmethyldiethoxysilane (APMDES) or N-cyclohexylaminomethyltriethoxysilane.

APTES can, for example, be purchased from Dow Corning under the name Xiameter OF S-6011 Silane or from Momentive Performance Materials under the name Silsoft A-1100 or from Shin-Etsu under the name KBE-903.

The compounds of formula (I) can also denote Dynasylan SIVO 210 or Dynasylan 1505, which are sold by Evonik.

The N-cyclohexylaminomethyltriethoxysilane can, for example, be purchased from Wacker under the name Geniosil XL 926.

Preferably, the alkoxysilane(s) of formula (I) are chosen from 3-aminopropyltriethoxysilane (APTES), 3-aminopropylmethyldiethoxysilane (APMDES), N-cyclohexylaminomethyltriethoxysilane and their mixtures, more preferentially 3-aminopropyltriethoxysilane (APTES).

The alkoxysilane(s) of formula (I), their oligomers and/or their mixtures are present in a total amount ranging from 0.1% to 30% by weight, preferably from 0.5% to 25% by weight, more preferentially from 1% to 20% by weight and better still from 5% to 20% by weight, with respect to the total weight of the composition.

Non Amino Silicone of Formula (II):

The process according to the invention comprises a composition comprising at least one non amino silicone of formula (II) below:

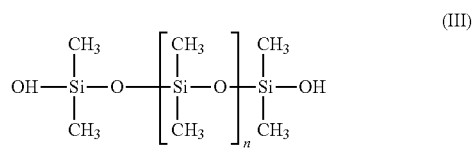

in which:
- $R_1$ represents an alkyl group having from 1 to 10 carbon atoms; or an alkoxy group having from 1 to 2 carbon atoms or an $-O_x-(X)_p-Si(OR_3)_3$ group with X representing a saturated divalent hydrocarbon radical having 1 carbon atom, $R_3$ representing an alkyl group having from 1 to 4 carbon atoms, x denoting an integer equal to 0 or 1 and p denoting an integer ranging from 0 to 4;
- $R_2$, which are identical or different, independently represents a hydroxyl group or an alkoxy group having from 1 to 2 carbon atoms;
- i denotes an integer ranging from 0 to 18, n denotes an integer ranging from 0 to 18 with n+i varying from 4 to 18.

Preferably, the non amino silicone(s) of formula (II) are such that:
- $R_1$ independently represents an alkyl group having from 1 to 10 carbon atoms, preferably from 1 to 4 carbon atoms, more preferentially a methyl;
- $R_2$ independently represents a hydroxyl group or an alkoxy group having from 1 to 2 carbon atoms;
- i denotes an integer ranging from 0 to 18, n denotes an integer ranging from 0 to 18 with n+i varying from 4 to 18.

More preferentially, the non amino silicone(s) of formula (II) are such that:
- $R_1$ independently represents an alkyl group having from 1 to 4 carbon atoms, more preferentially a methyl;
- $R_2$ independently represents a hydroxyl group;
- i denotes an integer ranging from 0 to 18, n denotes an integer ranging from 0 to 18 with n+i varying from 4 to 18.

"Non amino silicone" is understood to mean any silicone not comprising a primary, secondary or tertiary amine group or a quaternary ammonium group.

The non amino silicone(s) of formula (II) have a weight-average molecular weight of less than or equal to 1500 g/mol.

Preferably, the non amino silicone(s) of formula (II) have a weight-average molecular weight of less than or equal to 1300 g/mol.

Preferably, the non amino silicone(s) of formula (II) have a weight-average molecular weight ranging from 460 to 1500 g/mol, more preferentially from 500 to 1300 g/mol.

Preferably, the non amino silicone(s) of formula (II) capable of being employed in the context of the invention are represented by the following formula (III):

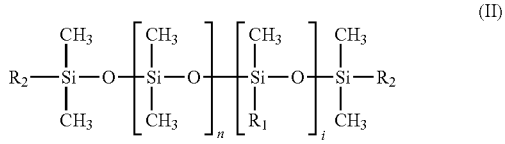

in which n denotes an integer ranging from 4 to 18.

Mention may be made, among the non amino silicones of formula (II), of polydimethylsiloxanes (PDMSs) having an alkoxy end functional group, such as those sold by Gelest under the reference DMS-XM11, or polydimethylsiloxanes (PDMSs) having a hydroxyl end functional group, such as those sold by Sigma Aldrich under the reference 481939 (Mn~550).

The non amino silicone(s) of formula (II) are present in a total amount ranging from 0.1% to 30% by weight, preferably from 0.5% to 25% by weight, more preferentially from 1% to 20% by weight, more preferentially still from 5% to 15% by weight, with respect to the total weight of the composition.

Weight Ratio:

The process according to the invention comprises a composition comprising an alkoxysilane(s) of formula (I)/non amino silicone(s) of formula (II) weight ratio varying from 95:5 to 5:95.

Preferably, the alkoxysilane(s) of formula (I)/non amino silicone(s) of formula (II) weight ratio varies from 90:10 to 10:90, preferentially from 80:20 to 20:80 and more preferentially from 70:30 to 30:70.

According to a specific embodiment, the APTES/non amino silicone(s) of formula (II) weight ratio varies from 90:10 to 10:90, preferentially from 80:20 to 20:80 and more preferentially from 70:30 to 30:70.

According to a specific embodiment, the APTES/non amino silicone(s) of formula (III) weight ratio varies from 90:10 to 10:90, more preferentially from 70:30 to 30:70.

Coloring Agent:

The process according to the invention comprises a composition comprising at least one coloring agent chosen from pigments, direct dyes and their mixtures.

Preferably, the composition according to the invention comprises one or more pigments.

Preferably, the coloring agent(s) are chosen from pigments.

"Pigment" is understood to mean any pigment which gives color to keratin materials. Their solubility in water at 25° C. and at atmospheric pressure (760 mmHg) is less than 0.05% by weight, and preferably less than 0.01% by weight.

The pigments which can be used are in particular chosen from the organic and/or mineral pigments known in the art, in particular those which are described in the Kirk-Othmer Encyclopedia of Chemical Technology and in Ullmann's Encyclopedia of Industrial Chemistry.

They can be natural, of natural origin, or non-natural.

These pigments can be provided in the pigment powder or paste form. They can be coated or uncoated.

The pigments can be chosen, for example, from mineral pigments, organic pigments, lakes, special effect pigments, such as pearlescent agents or glitter, and their mixtures.

The pigment can be a mineral pigment. Mineral pigment is understood to mean any pigment which corresponds to the definition of Ullmann's Encyclopedia in the Inorganic Pigments chapter. Mention may be made, among the mineral pigments of use in the present invention, of iron oxides, chromium oxides, manganese violet, ultramarine blue, chromium hydrate, ferric blue and titanium oxide.

The pigment can be an organic pigment. "Organic pigment" is understood to mean any pigment which corresponds to the definition of Ullmann's Encyclopedia in the Organic Pigments chapter.

The organic pigment can in particular be chosen from nitroso, nitro, azo, xanthene, pyrene, quinoline, anthraquinone, triphenylmethane, fluorane, phthalocyanine, metal-complex type, isoindolinone, isoindoline, quinacridone, perinone, perylene, diketopyrrolopyrrole, indigo, thioindigo, dioxazine and quinophthalone compounds.

In particular, the white or colored organic pigments can be chosen from carmine, carbon black, aniline black, azo yellow, quinacridone, phthalocyanine blue, the blue pigments codified in the Color Index under the references CI 42090, 69800, 69825, 74100, 74160, the yellow pigments codified in the Color Index under the references CI 11680, 11710, 19140, 20040, 21100, 21108, 47000, 47005, the green pigments codified in the Color Index under the references CI 61565, 61570, 74260, the orange pigments codified in the Color Index under the references CI 11725, 45370, 71105, the red pigments codified in the Color Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives such as are described in the patent FR 2 679 771.

Mention may also be made, by way of example, of pigment pastes of organic pigments, such as the products sold by Hoechst under the names:
  Cosmenyl Yellow 10G: Pigment Yellow 3 (CI 11710);
  Cosmenyl Yellow G: Pigment Yellow 1 (CI 11680);
  Cosmenyl Orange GR: Pigment Orange 43 (CI 71105);
  Cosmenyl Red R: Pigment Red 4 (CI 12085);
  Cosmenyl Carmine FB: Pigment Red 5 (CI 12490);
  Cosmenyl Violet RL: Pigment Violet 23 (CI 51319);
  Cosmenyl Blue A2R: Pigment Blue 15.1 (CI 74160);
  Cosmenyl Green GG: Pigment Green 7 (CI 74260);
  Cosmenyl Black R: Pigment Black 7 (CI 77266).

The pigments in accordance with the invention can also be in the form of composite pigments, such as are described in the patent EP 1 184 426. These composite pigments can be composed in particular of particles including an inorganic core, at least one binder providing the fixing of the organic pigments to the core, and at least one organic pigment which at least partially covers the core.

The organic pigment can also be a lake. Lake is understood to mean dyes adsorbed onto insoluble particles, the assembly thus obtained remaining insoluble during use.

The inorganic substrates onto which the dyes are adsorbed are, for example, alumina, silica, calcium sodium borosilicate or calcium aluminum borosilicate, and aluminum.

Mention may be made, among the dyes, of carminic acid. Mention may also be made of the dyes known under the following names: D&C Red 21 (CI 45380), D&C Orange 5 (CI 45370), D&C Red 27 (CI 45410), D&C Orange 10 (CI 45425), D&C Red 3 (CI 45430), D&C Red 4 (CI 15510), D&C Red 33 (CI 17200), D&C Yellow 5 (CI 19140), D&C Yellow 6 (CI 15985), D&C Green (CI 61570), D&C Yellow 1 O (CI 77002), D&C Green 3 (CI 42053), D&C Blue 1 (CI 42090).

Mention may be made, as an example of a lake, of the product known under the following name: D&C Red 7 (CI 15850:1).

The pigment can also be a special effect pigment. Special effect pigments is understood to mean pigments which create in a general way a colored appearance (characterized by a certain shade, a certain vividness and a certain brightness) which is nonuniform and which changes as a function of the conditions of observation (light, temperature, angles of observation, and the like). They thereby contrast with colored pigments, which provide a conventional uniform opaque, semitransparent or transparent shade.

Several types of special effect pigments exist: those having a low refractive index, such as fluorescent or photochromic pigments, and those having a higher refractive index, such as pearlescent agents, interference pigments or glitters.

Mention may be made, as examples of special effect pigments, of pearlescent pigments, such as mica coated with titanium or with bismuth oxychloride, colored pearlescent pigments, such as mica covered with titanium and with iron oxides, mica covered with iron oxide, mica covered with titanium and in particular with ferric blue or with chromium oxide, mica covered with titanium and with an organic pigment as defined above, and also pearlescent pigments based on bismuth oxychloride. Mention may be made, as pearlescent pigments, of the pearlescent agents Cellini sold by BASF (mica-TiO$_2$-lake), Prestige sold by Eckart (mica-TiO$_2$), Prestige Bronze sold by Eckart (mica-Fe$_2$O$_3$) or Colorona sold by Merck (mica-TiO$_2$—Fe$_2$O$_3$).

Mention may also be made of gold-colored pearlescent agents sold in particular by BASF under the names Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by BASF under the name Super Bronze (Cloisonne); orange pearlescent agents sold in particular by BASF under the names Orange 363C (Cloisonne) and Orange MCR 101 (Cosmica) and by Merck under the names Passion Orange (Colorona) and Matte Orange (17449) (Microna); brown-colored pearlescent agents sold in particular by BASF under the names Nu-Antique Copper 340XB (Cloisonne) and Brown CL4509 (Chromalite); pearlescent agents with a copper glint sold in particular by BASF under the name Copper 340A (Timica); pearlescent agents with a red glint sold in particular by Merck under the name Sienna Fine (17386) (Colorona); pearlescent agents with a yellow glint sold in particular by BASF under the name Yellow (4502) (Chromalite); red-colored pearlescent agents with a gold glint sold in particular by BASF under the name Sunstone G012 (Gemtone); pink pearlescent agents sold in particular by BASF under the name Tan Opale G005 (Gemtone); black pearlescent agents with a gold glint sold in particular by BASF under the name Nu-Antique Bronze 240 AB (Timica), blue pearlescent agents sold in particular by Merck under the name Matte Blue (17433) (Microna), white pearlescent agents with a silvery glint sold in particular by Merck under the name Xirona Silver, and golden green pinkish orangey pearlescent agents sold in particular by Merck under the name Indian Summer (Xirona), and their mixtures.

Mention may also be made, still as examples of pearlescent agents, of particles comprising a borosilicate substrate coated with titanium oxide.

Particles having a glass substrate coated with titanium oxide are sold in particular under the name Metashine MC1080RY by Toyal.

Finally, mention may also be made, as examples of pearlescent agents, of polyethylene terephthalate glitter, in particular that sold by Meadowbrook Inventions under the name Silver 1P 0.004×0.004 (silver glitter). It is also possible to envisage multilayer pigments based on synthetic substrates, such as alumina, silica, calcium sodium borosilicate, calcium aluminum borosilicate and aluminum.

The special effect pigments can also be chosen from reflective particles, that is to say in particular particles having a size, a structure, in particular a thickness of the layer or layers of which it is composed and their physical and chemical nature, and a surface condition which allow them to reflect incident light. This reflection may, if appropriate, have an intensity sufficient to create, at the surface of the composition or of the mixture, when the latter is applied to the support to be made up, highlight points visible to the naked eye, that is to say more luminous points which contrast with their environment by appearing to sparkle.

The reflective particles can be selected so as not to detrimentally affect, to a significant extent, the coloring effect generated by the coloring agents which are combined with them and more particularly so as to optimize this effect in terms of color rendition. They can more particularly have a yellow, pink, red, bronze, orangey, brown, gold and/or coppery color or glint.

These particles can exhibit varied forms and can in particular be in the platelet or globular form, especially the spherical form.

The reflective particles, whatever their form, may or may not exhibit a multilayer structure and, in the case of a multilayer structure, may exhibit, for example, at least one layer of uniform thickness, in particular of a reflective material.

When the reflective particles do not exhibit a multilayer structure, they can be composed, for example, of metal oxides, in particular of titanium or iron oxides obtained synthetically.

When the reflective particles exhibit a multilayer structure, they can, for example, comprise a natural or synthetic substrate, in particular a synthetic substrate, at least partially coated with at least one layer of a reflective material, in particular of at least one metal or metal material. The substrate can be made of one or more organic and/or inorganic materials.

More particularly, it can be chosen from glasses, ceramics, graphite, metal oxides, aluminas, silicas, silicates, in particular aluminosilicates and borosilicates, synthetic mica and their mixtures, this list not being limiting.

The reflective material can comprise a layer of metal or of a metal material.

Reflective particles are described in particular in the documents JP-A-09188830, JP-A-10158450, JP-A-10158541, JP-A-07258460 and JP-A-05017710.

Mention may also be made, still by way of example of reflective particles comprising an inorganic substrate coated with a layer of metal, of the particles comprising a borosilicate substrate coated with silver.

Particles comprising a glass substrate coated with silver, in the form of platelets, are sold under the name Microglass Metashine REFSX 2025 PS by Toyal. Particles comprising a glass substrate coated with nickel/chromium/molybdenum alloy are sold under the names Crystal Star GF 550 and GF 2525 by this same company.

Use may also be made of particles comprising a metal substrate, such as silver, aluminum, iron, chromium, nickel, molybdenum, gold, copper, zinc, tin, magnesium, steel, bronze or titanium, said substrate being coated with at least one layer of at least one metal oxide, such as titanium oxide, aluminum oxide, iron oxide, cerium oxide, chromium oxide, silicon oxides and their mixtures.

Mention may be made, by way of examples, of aluminum powder, bronze powder or copper powder coated with $SiO_2$ sold under the name Visionaire by Eckart.

Mention may also be made of pigments with an interference effect which are not attached to a substrate, such as liquid crystals (Helicones HC from Wacker) or interference holographic glitter (Geometric Pigments or Spectra f/x from Spectratek). Special effect pigments also comprise fluorescent pigments, whether these are substances which are fluorescent in daylight or which produce an ultraviolet fluorescence, phosphorescent pigments, photochromic pigments, thermochromic pigments and quantum dots, for example sold by Quantum Dots Corporation.

The variety of the pigments which can be used in the present invention makes it possible to obtain a rich palette of colors and also specific optical effects, such as metallic effects or interference effects.

The size of the pigment used in the composition according to the present invention is generally between 10 nm and 200 µm, preferably between 20 nm and 80 µm and more preferentially between 30 nm and 50 µm.

The pigments can be dispersed in the composition by virtue of a dispersing agent.

The dispersing agent serves to protect the dispersed particles from the agglomeration or flocculation thereof. This dispersing agent can be a surfactant, an oligomer, a polymer or a mixture of several of them carrying one or more functionalities having a strong affinity for the surface of the particles to be dispersed. In particular, they can become attached physically or chemically to the surface of the pigments. These dispersants additionally exhibit at least one functional group compatible with or soluble in the continuous medium. Use is made in particular of esters of 12-hydroxystearic acid, in particular, and of $C_8$ to $C_{20}$ fatty acid and of polyol, for instance glycerol or diglycerol, such as poly(12-hydroxystearic acid) stearate with a molecular weight of approximately 750 g/mol, such as that sold under the name of Solsperse 21 000 by Avecia, polyglyceryl-2 dipolyhydroxystearate (CTFA name), sold under the reference Dehymuls PGPH by Henkel, or polyhydroxystearic acid, such as that sold under the reference Arlacel P100 by Uniqema, and their mixtures.

Mention may be made, as other dispersant which can be used in the compositions of the invention, of the quaternary ammonium derivative of polycondensed fatty acids, such as Solsperse 17 000, sold by Avecia, and polydimethylsiloxane/oxypropylene mixtures, such as those sold by Dow Corning under the references DC2-5185 and DC2-5225 C.

The pigments used in the composition can be surface-treated with an organic agent.

Thus, the pigments surface-treated beforehand of use in the context of the invention are pigments which have been completely or partially subjected to a surface treatment of chemical, electronic, electrochemical, mechanochemical or mechanical nature with an organic agent, such as those which are described in particular in Cosmetics and Toiletries, February 1990, Vol. 105, pages 53-64, before being dispersed in the composition in accordance with the invention. These organic agents can, for example, be chosen from waxes, for example carnauba wax and beeswax; fatty acids, fatty alcohols and their derivatives, such as stearic acid, hydroxystearic acid, stearyl alcohol, hydroxystearyl alcohol and lauric acid and their derivatives; anionic surfactants; lecithins; sodium, potassium, magnesium, iron, titanium, zinc or aluminum salts of fatty acids, for example aluminum stearate or laurate; metal alkoxides; polyethylene; (meth) acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; or fluorosilicone compounds.

The surface-treated pigments of use in the composition may also have been treated with a mixture of these compounds and/or may have undergone several surface treatments.

The surface-treated pigments of use in the context of the present invention can be prepared according to surface treatment techniques well known to a person skilled in the art or found as such commercially.

Preferably, the surface-treated pigments are covered with an organic layer.

The organic agent with which the pigments are treated can be deposited on the pigments by evaporation of solvent, chemical reaction between the molecules of the surface agent or creation of a covalent bond between the surface agent and the pigments.

The surface treatment can thus be carried out, for example, by chemical reaction of a surface agent with the surface of the pigments and creation of a covalent bond between the surface agent and the pigments or fillers. This method is described in particular in the patent U.S. Pat. No. 4,578,266.

Preferably, use will be made of an organic agent covalently bonded to the pigments.

The agent for the surface treatment can represent from 0.1% to 50% by weight of the total weight of the surface-treated pigment, preferably from 0.5% to 30% by weight and more preferentially still from 1% to 20% by weight of the total weight of the surface-treated pigment.

Preferably, the surface treatments of the pigments are chosen from the following treatments:
- a PEG-silicone treatment, such as the AQ surface treatment sold by LCW;
- a methicone treatment, such as the SI surface treatment sold by LCW;
- a dimethicone treatment, such as the Covasil 3.05 surface treatment sold by LCW;
- a dimethicone/trimethylsiloxysilicate treatment, such as the Covasil 4.05 surface treatment sold by LCW;
- a magnesium myristate treatment, such as the MM surface treatment sold by LCW;
- an aluminum dimyristate treatment, such as the MI surface treatment sold by Miyoshi;
- a perfluoropolymethylisopropyl ether treatment, such as the FHC surface treatment sold by LCW;
- an isostearyl sebacate treatment, such as the HS surface treatment sold by Miyoshi;
- a perfluoroalkyl phosphate treatment, such as the PF surface treatment sold by Daito;
- an acrylate/dimethicone copolymer and perfluoalkyl phosphate treatment, such as the FSA surface treatment sold by Daito;
- a polymethylhydrosiloxane/perfluoroalkyl phosphate treatment, such as the FS01 surface treatment sold by Daito;
- an acrylate/dimethicone copolymer treatment, such as the ASC surface treatment sold by Daito;
- an isopropyl titanium triisostearate treatment, such as the ITT surface treatment sold by Daito;
- an acrylate copolymer treatment, such as the APD surface treatment sold by Daito;
- a perfluoroalkyl phosphate/isopropyl titanium triisostearate treatment, such as the PF+ITT surface treatment sold by Daito.

According to a specific embodiment of the invention, the dispersing agent is present with organic or inorganic pigments in particulate form of submicronic size in the dye composition.

"Submicronic" is understood to mean pigments, the particle size of which has been micronized by a micronization method and the mean particle size of which is less than a micrometer (µall), in particular between 0.1 and 0.9 µm, and preferably between 0.2 and 0.6 µm.

According to one embodiment, the dispersing agent and the pigment(s) are present in an amount (dispersant:pigment) of between 1:4 and 4:1, particularly between 1.5:3.5 and 3.5:1 or better still between 1.75:3 and 3:1.

The dispersing agent(s) can thus have a silicone backbone, such as silicone polyether and dispersing agents of aminosilicone type other than the alkoxysilanes described above. Mention may be made, among the suitable dispersing agents, of:
- aminosilicones, i.e. silicones comprising one or more amino groups, such as those sold under the names and references: Byk LPX 21879, by Byk, GP-4, GP-6, GP-344, GP-851, GP-965, GP-967 and GP-988-1, sold by Genesee Polymers,
- silicone acrylates, such as Tego® RC 902, Tego® RC 922, Tego® RC 1041 and Tego® RC 1043, sold by Evonik,
- polydimethylsiloxane (PDMS) silicones having carboxyl groups, such as X-22162 and X-22370, sold by Shin-Etsu, epoxy silicones, such as GP-29, GP-32, GP-502, GP-504, GP-514, GP-607, GP-682 and GP-695, sold by Genesee Polymers, or Tego® RC 1401, Tego® RC 1403 and Tego® RC 1412, sold by Evonik.

According to a specific embodiment, the dispersing agent(s) are of aminosilicone type, other than the alkoxysilanes described above, and are cationic.

Preferably, the pigment(s) is (are) chosen from mineral, mixed mineral-organic or organic pigments.

In one alternative form of the invention, the pigment(s) according to the invention are organic pigments, preferentially organic pigments surface-treated with an organic agent chosen from silicone compounds. In another alternative form of the invention, the pigment(s) according to the invention are mineral pigments.

The composition according to the invention can comprise one or more direct dye(s).

"Direct dye" is understood to mean natural and/or synthetic dyes, other than oxidation dyes. These are dyes that will diffuse superficially over the fiber.

They can be ionic or nonionic, preferably anionic, cationic or nonionic.

Examples of suitable direct dyes which may be mentioned comprise azo direct dyes; (poly)methine dyes, such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of the formulae (IV) and (V), and of the azo cationic dyes (VI) and (VII) below:

Het⁺-C(R=N—N(Rb)—Ar Q- (IV)

Het⁺-N(Ra)—N=C(Rb)—Ar Q- (V)

Het⁺-N=N—Ar Q- (VI)

Ar⁺—N=N—Ar"Q- (VII)

in which formulae (IV) to (VII):

Het⁺ represents a cationic heteroaryl radical, preferentially having an endocyclic cationic charge, such as imidazolium, indolium or pyridinium, which is optionally substituted, preferentially by at least one $(C_1-C_8)$ alkyl group, such as methyl;

Ar⁺ represents an aryl radical, such as phenyl or naphthyl, having an exocyclic cationic charge, preferentially ammonium, particularly tri$(C_1-C_8)$alkylammonium, such as trimethylammonium;

Ar represents an aryl group, in particular phenyl, which is optionally substituted, preferentially by one or more electron-donating groups, such as i) optionally substituted $(C_1-C_8)$alkyl, ii) optionally substituted $(C_1-C_8)$ alcoxy, iii) (di)$(C_1-C_8)$(alkyl)amino optionally substituted on the alkyl group(s) by a hydroxyl group, iv) aryl$(C_1-C_8)$alkylamino, v) optionally substituted N—$(C_1-C_8)$alkyl-N-aryl$(C_1-C_8)$alkylamino or else Ar represents a julolidine group;

Ar" represents an optionally substituted (hetero)aryl group, such as phenyl or pyrazolyl, which are optionally substituted, preferentially by one or more $(C_1-C_8)$ alkyl, hydroxyl, (di)$(C_1-C_8)$(alkyl)amino, $(C_1-C_8)$ alkoxy or phenyl groups;

Ra and Rb, which are identical or different, represent a hydrogen atom or a $(C_1-C_8)$alkyl group which is optionally substituted, preferentially by a hydroxyl group; or else the substituent Ra with a Het⁺ substituent and/or Rb with an Ar substituent form, together with the atoms which carry them, a (hetero)cycloalkyl; in particular, Ra and Rb represent a hydrogen atom or a $(C_1-C_4)$alkyl group optionally substituted by a hydroxyl group;

Q⁻ represents an organic or inorganic anionic counterion, such as a halide or an alkyl sulfate.

In particular, mention may be made of the azo and hydrazono direct dyes having an endocyclic cationic charge of formulae (IV) to (VII) as defined above, More particularly of the cationic direct dyes having an endocyclic cationic charge described in the patent applications WO 95/15144, WO 95/01772 and EP 714 954, preferentially the following direct dyes:

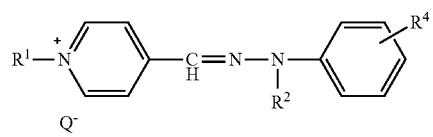
(VIII)

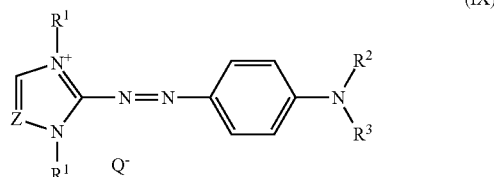
(IX)

in which formulae (VIII) and (IX):

R¹ represents a $(C_1-C_4)$alkyl group, such as methyl;

R² and R³, which are identical or different, represent a hydrogen atom or a $(C_1-C_4)$alkyl group, such as methyl; and R⁴ represents a hydrogen atom or an electron-donating group, such as optionally substituted $(C_1-C_8)$alkyl, optionally substituted $(C_1-C_8)$alkoxy, or (di)$(C_1-C_8)$ (alkyl)amino optionally substituted on the alkyl group(s) by a hydroxyl group; in particular, R⁴ is a hydrogen atom;

Z represents a CH group or a nitrogen atom, preferentially CH,

Q⁻ is an anionic counterion as defined above, particularly a halide, such as chloride, or an alkyl sulfate, such as methyl sulfate or mesylate.

In particular, the dyes of formulae (VIII) and (IX) are chosen from Basic Red 51, Basic Yellow 87 and Basic Orange 31 or their derivatives with Q⁻ an anionic counterion as defined above, particularly a halide, such as chloride, or an alkyl sulfate, such methyl sulfate or mesylate.

The direct dyes can be chosen from anionic direct dyes. The anionic direct dyes of the invention are dyes commonly referred to as "acid" direct dyes for their affinity for alkaline substances. "Anionic direct dye" is understood to mean any direct dye comprising in its structure at least one $CO_2R$ or $SO_3R$ substituent with R denoting a hydrogen atom or a cation originating from a metal or from an amine, or an ammonium ion. The anionic dyes can be chosen from acid nitro direct dyes, acid azo dyes, acid azine dyes, acid triarylmethane dyes, acid indoamine dyes, acid anthraquinone dyes, indigoids and acid natural dyes.

Mention may be made, as acid dyes according to the invention, of the dyes of following formulae (X), (X'), (XI), (XI'), (XII), (XII'), (XIII), (XIII'), (XIV), (XV), (XVI) and (XVII):

a) diaryl anionic azo dyes of formula (X) or (X'):

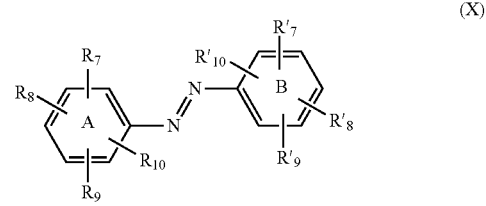
(X)

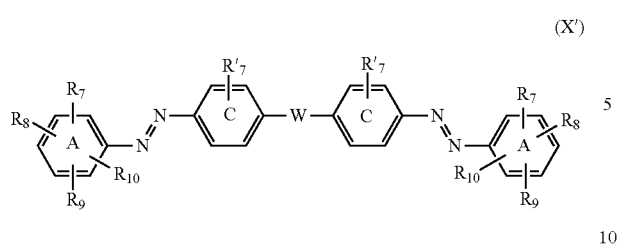

(X')

in which formulae (X) and (X'):

$R_7$, $R_8$, $R_9$, $R_{10}$, $R'_7$, $R'_8$, $R'_9$ and $R'_{10}$, which are identical or different, represent a hydrogen atom or a group chosen from:
alkyl;
alkoxy, alkylthio;
hydroxyl, mercapto;
nitro, nitroso;
R°—C(X)—X'—, R°—X'—C(X)—, R°—X'—C(X)—X"— with R° representing a hydrogen atom or an alkyl or aryl group; X, X' and X", which are identical or different, representing an oxygen or sulfur atom or NR with R representing a hydrogen atom or an alkyl group;
$M^+(O)_2S(O^-)$— with $M^+$ representing a hydrogen atom or a cationic counterion;
$M^+(O)CO^-$— with $M^+$ as defined above;
R"—S(O)$_2$—, with R" representing a hydrogen atom or an alkyl, aryl, (di)(alkyl)amino or aryl(alkyl)amino group; preferentially, a phenylamino or phenyl group;
R'"—S(O)$_2$—X'— with R'" representing an alkyl group or an aryl group which is optionally substituted, and X' as defined above;
(di)(alkyl)amino;
aryl(alkyl)amino, optionally substituted by one or more groups chosen from i) nitro; ii) nitroso; iii) $M^+(O)_2S(O^-)$— and iv) alkoxy, with $M^+$ as defined above;
optionally substituted heteroaryl; preferentially a benzothiazolyl group;
cycloalkyl; in particular cyclohexyl,
Ar—N=N—, with Ar representing an optionally substituted aryl group; preferentially, a phenyl optionally substituted by one or more alkyl, $M^+(O)_2S(O^-)$— or phenylamino groups;
or else two contiguous groups, $R_7$ with $R_8$ or $R_8$ with $R_9$ or $R_9$ with $R_{10}$, together form a fused benzo group A'; and $R'_7$ with $R'_8$ or $R'_8$ with $R'_9$ or $R'_9$ with $R'_{10}$ together form a fused benzo group B'; with A' and B' optionally substituted by one or more groups chosen from i) nitro; ii) nitroso; iii) $M^+(O)_2S(O^-)$—; iv) hydroxyl; v) mercapto; vi) (di)(alkyl)amino; vii) R°—C(X)—X'—; viii) R°—X'—C(X)—; ix) R°—X'—C(X)—X"—; x) Ar—N=N— and xi) aryl(alkyl)amino which is optionally substituted; with $M^+$, R°, X, X', X" and Ar as defined above;

W represents a sigma a bond, an oxygen or sulfur atom or a divalent radical i) —NR—, with R as defined above, or ii) methylene —C(Ra)(Rb)—, with Ra and Rb, which are identical or different, representing a hydrogen atom or an aryl group, or else Ra and Rb form, together with the carbon atom which carries them, a spirocycloalkyl; preferentially, W represents a sulfur atom or Ra and Rb together form a cyclohexyl;

it being understood that the formulae (X) and (X') comprise at least one sulfonate radical $M^+(O)_2S(O^-)$— or carboxylate radical $M^+(O)CO^-$— on one of the rings A, A', B, B' or C; preferentially, sodium sulfonate;

Mention may be made, as examples of dyes of formula (X), of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment Red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and mention may be made, as examples of dyes of formula (X'), of: Acid Red 111, Acid Red 134 or Acid Yellow 38;

b) pyrazolone anionic azo dyes of formulae (XI) and (XI'):

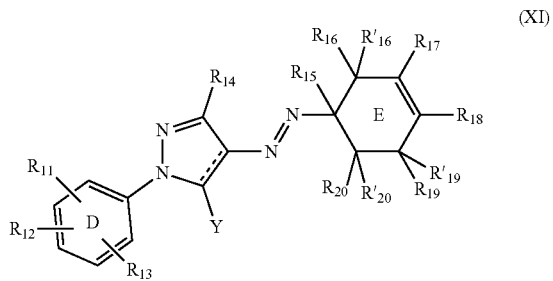

(XI)

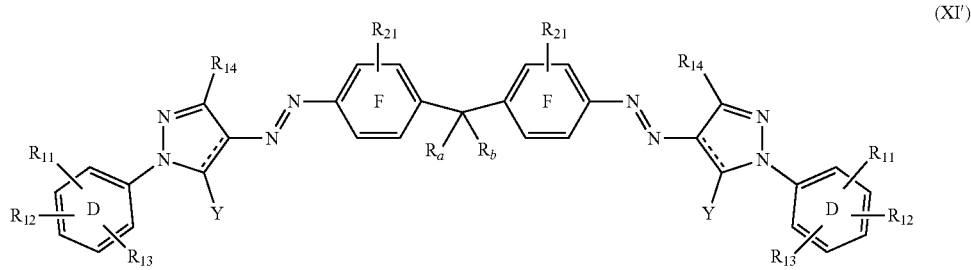

(XI')

in which formulae (XI) and (XI'):

R$_{11}$, R$_{12}$ and R$_{13}$, which are identical or different, represent a hydrogen atom, a halogen atom, an alkyl group or an M$^+$(O)$_2$S(O$^-$)— group, with M$^+$ as defined above;

R$_{14}$ represents a hydrogen atom, an alkyl group or an M$^+$C(O)O$^-$— group, with M$^+$ as defined above;

R$_{15}$ represents a hydrogen atom;

R$_{16}$ represents an oxo group, in which case R'$_{16}$ is absent, or else R$_{15}$ with R$_{16}$ together form a double bond;

R$_{17}$ and R$_{18}$, which are identical or different, represent a hydrogen atom or a group chosen from:
  M$^+$(O)$_2$S(O$^-$)—, with M+ as defined above;
  Ar—O—S(O)$_2$—, with Ar representing an optionally substituted aryl group; preferentially a phenyl optionally substituted by one or more alkyl groups;

R$_{19}$ and R$_{20}$ together form either a double bond or an optionally substituted benzo group D';

R'$_{16}$, R'$_{19}$ and R'$_{20}$, which are identical or different, represent a hydrogen atom, an alkyl group or a hydroxyl group;

R$_{21}$ represents a hydrogen atom, an alkyl group or an alkoxy group;

R$_a$ and R$_b$, which are identical or different, are as defined above; preferentially, R$_a$ represent a hydrogen atom and Rb represents an aryl group;

Y represents either a hydroxyl group or an oxo group;

- - - - represents a single bond when Y is an oxo group and represents a double bond when Y represents a hydroxyl group;

it being understood that the formulae (XI) and (XI') comprise at least one sulfonate radical M$^+$(O)$_2$S(O$^-$)— or one carboxylate radical M$^+$C(O)O$^-$— on one of the rings D or E; preferentially, sodium sulfonate;

Mention may be made, as examples of dyes of formula (XI), of: Acid Red 195, Acid Yellow 23, Acid Yellow 27 or Acid Yellow 76, and mention may be made, as examples of dyes of formula (XI'), of: Acid Yellow 17;

c) anthraquinone dyes of formulae (XII) and (XII'):

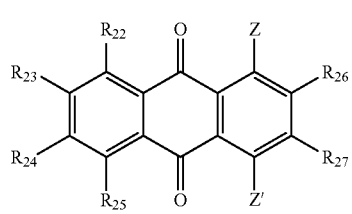

(XII)

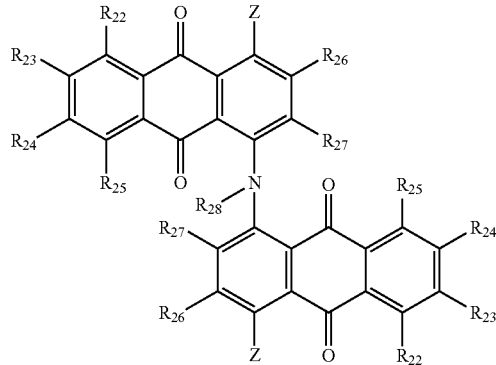

(XII')

in which formulae (XII) and (XII'):

R$_{22}$, R$_{23}$, R$_{24}$, R$_{25}$, R$_{26}$ and R$_{27}$, which are identical or different, represent a hydrogen atom, a halogen atom or a group chosen from:
  alkyl;
  hydroxyl, mercapto;
  alkoxy, alkylthio;
  optionally substituted aryloxy ou arylthio, preferentially substituted by one or more groups chosen from alkyl and M$^+$(O)$_2$S(O$^-$)—, with M$^+$ as defined above;
  aryl(alkyl)amino optionally substituted by one or more groups chosen from alkyl and M$^+$(O)$_2$S(O)—, with M$^+$ as defined above;
  (di)(alkyl)amino;
  (di)(hydroxyalkyl)amino;
  M$^+$(O)$_2$S(O)—, with M$^+$ as defined above;

Z' represents a hydrogen atom or an NR$_{28}$R$_{29}$ group with R$_{28}$ and R$_{29}$, which are identical or different, representing a hydrogen atom or a group chosen from:
  alkyl;
  (poly)hydroxyalkyl, such as hydroxyethyl;
  aryl optionally substituted by one or more groups, particularly i) alkyl, such as methyl, n-dodecyl or n-butyl; ii) M$^+$(O)$_2$S(O)—, with M$^+$ as defined above; iii) R$^o$—C(X)—X'—, R$^o$—X'—C(X)— or R$^o$—X'—C(X)—X"—, with R$^o$, X, X' and X" as defined above; preferentially, R$^o$ represents an alkyl group;
  cycloakyl; in particular cyclohexyl;

Z represents a group chosen from hydroxyl and NR'$_{28}$R'$_{29}$ with R'$_{28}$ and R'$_{29}$, which are identical or different, representing the same atoms or groups as R$_{28}$ and R$_{29}$ as defined above;

it being understood that the formulae (XII) and (XII') comprise at least one sulfonate radical M$^+$(O)$_2$S(O$^-$)— or one carboxylate radical M$^+$C(O)O$^-$; preferentially, sodium sulfonate;

Mention may be made, as examples of dyes of formula (XII), of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3 or Ext. Violet No. 2; and mention may be made, as an example of dyes of formula (XII'), of: Acid Black 48;

d) nitro dyes of formulae (XIII) and (XIII'):

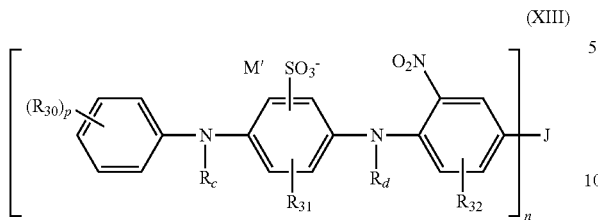

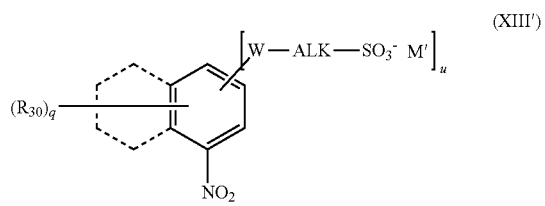

in which formulae (XIII) and (XIII'):
$R_{30}$, $R_{31}$ and $R_{32}$, which are identical or different, represent a hydrogen atom, a halogen atom or a group chosen from:
  alkyl;
  alkoxy optionally substituted by one or more hydroxyl groups, or alkylthio optionally substituted by one or more hydroxyl groups;
  hydroxyl, mercapto;
  nitro, nitroso;
  polyhaloalkyl;
  $R^\circ$—C(X)—X'—, $R^\circ$—X'—C(X)— or $R^\circ$—X'—C(X)—X"—, with $R^\circ$, X, X' and X" as defined above;
  $M^+(O)_2S(O^-)$—, with $M^+$ as defined above;
  $M^+(O)CO^-$—, with $M^+$ as defined above;
  (di)(alkyl)amino;
  (di)(hydroxyalkyl)amino;
  heterocycloalkyl, such as piperidino, piperazino or morpholino; in particular, $R_{30}$, $R_{31}$ and $R_{32}$ represent a hydrogen atom;
It, and Rd, which are identical or different, represent a hydrogen atom or an alkyl group;
W is as defined above; W represents in particular an —NH— group;
ALK represents a linear or branched divalent $C_1$-$C_6$ alkylene group; in particular, ALK represents a —CH$_2$—CH$_2$— group;
n has a value of 1 or 2;
p represents an integer between 1 and 5 inclusive;
q represents an integer between 1 and 4 inclusive;
u has a value of 0 or 1;
when n has a value of 1, J represents a nitro or nitroso group; in particular a nitro group;
when n has a value of 2, J represents an oxygen or sulfur atom or a divalent —S(O)$_m$— radical with m representing an integer which is 1 or 2; preferentially, J represents an —SO$_2$— radical;
M' represents a hydrogen atom or a cationic counterion;

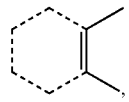

which is present or absent, represents a benzo group optionally substituted by one or more $R_{30}$ groups as defined above;
it being understood that the formulae (XIII) and (XIII') comprise at least one sulfonate radical $M^+(O)_2S(O^-)$— or one carboxylate radical $M^+C(O)O^-$—; preferentially, sodium sulfonate.

Mention may be made, as examples of dyes of formula (XIII), of: Acid Brown 13 and Acid Orange 3; mention may be made, as examples of dyes of formula (XIII'), of: Acid Yellow 1, sodium salt of 2,4-dinitro-1-naphthol-7-sulfonic acid, 2-piperidino-5-nitrobenzenesulfonic acid, 2-(4'-N,N-(2"-hydroxyethyl)amino-2'-nitro)aniline ethane sulfonic acid, 4-β-hydroxyethylamino-3-nitrobenzenesulfonic acid; Ext. D&C Yellow 7;

e) triarylmethane dyes of formula (XIV):

(XIV)

in which formula (XIV):
$R_{33}$, $R_{34}$, $R_{35}$ and $R_{36}$, which are identical or different, represent a hydrogen atom or a group chosen from alkyl, optionally substituted aryl and optionally substituted aralkyl; particularly, an alkyl or benzyl group optionally substituted by an $M^+(O)_mS(O^-)$— group, with $M^+$ and m as defined above; $R_{37}$, $R_{38}$, $R_{39}$, $R_{40}$, $R_{41}$, $R_{42}$, $R_{43}$ and $R_{44}$, which are identical or different, represent a hydrogen atom or a group chosen from:
  alkyl;
  alkoxy, alkylthio;
  (di)(alkyl)amino;
  hydroxyl, mercapto;
  nitro, nitroso;
  $R^\circ$—C(X)—X'—, $R^\circ$—X'—C(X)— or $R^\circ$—X'—C(X)—X"—, with $R^\circ$ representing a hydrogen atom, an alkyl group or an aryl group and X, X' and X", which are identical or different, representing an oxygen or sulfur atom or NR with R representing a hydrogen atom or an alkyl group;
  $M^+(O)_2S(O^-)$—, with $M^+$ representing a hydrogen atom or a cationic counterion;
  $M^+(O)CO^-$—, with $M^+$ as defined above;
  or else two contiguous groups, $R_{41}$ with $R_{42}$ or $R_{42}$ with $R_{43}$ or $R_{43}$ with $R_{44}$, together form a fused benzo group: I'; with I' optionally substituted by one or more groups chosen from i) nitro; ii) nitroso; iii) $M^+(O)_2S(O^-)$—; iv) hydroxyl; v) mercapto; vi) (di)

(alkyl)amino; vii) R°—C(X)—X'—; viii) R°—X'—C(X)—; ix) R°—X'—C(X)—X"—; with M⁺, R°, X, X', X" as defined above; in particular, $R_{37}$ to $R_{40}$ represent a hydrogen atom and $R_{41}$ to $R_{44}$, which are identical or different, represent a hydroxyl or M⁺(O)₂S(O⁻)— group; and, when $R_{43}$ with $R_{44}$ together form a benzo group, it is preferentially substituted by an (O)₂S(O)— group;

it being understood that at least one of the rings G, H, I or I' comprises at least one sulfonate radical (O)₂S(O⁻)— or one carboxylate radical C(O)O⁻—; preferentially sulfonate;

Mention may be made, as examples of dyes of formula (XIV), of: Acid Blue 1, Acid Blue 3, Acid Blue 7, Acid Blue 9, Acid Violet 49, Acid Green 3, Acid Green 5 and Acid Green 50;

e) xanthene-based dyes of formula (XV):

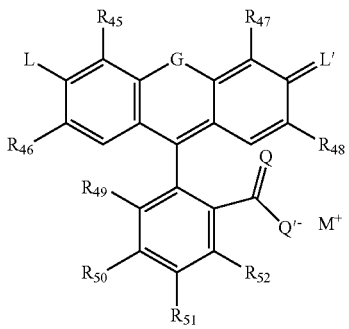

(XV)

in which formula (XV):

$R_{45}$, $R_{46}$, $R_{47}$ and $R_{48}$, which are identical or different, represent a hydrogen atom or a halogen atom;

$R_{49}$, $R_{50}$, $R_{51}$ and $R_{52}$, which are identical or different, represent a hydrogen atom, a halogen atom or a group chosen from:
alkyl;
alkoxy, alkylthio;
hydroxyl, mercapto;
nitro, nitroso;
M⁺(O)₂S(O⁻)—, with M⁺ representing a hydrogen atom or a cationic counterion;
M⁺(O)CO⁻—, with M⁺ as defined above;

particularly, $R_{53}$ $R_{54}$, $R_{55}$ and $R_{48}$ represent a hydrogen atom or a halogen atom;

G represents an oxygen or sulfur atom or an NR$_e$ group, with R$_e$ as defined above; in particular, G represents an oxygen atom;

L represents an alkoxide M⁺O⁻; a thioalkoxide M⁺S⁻ or an NR$_f$ group, with R$_f$ representing a hydrogen atom or an alkyl group and M⁺ as defined above; M⁺ is in particular sodium or potassium;

L' represents an oxygen or sulfur atom or an ammonium group: N⁺R$_f$R$_g$, with R$_f$ and R$_g$, which are identical or different, representing a hydrogen atom, an alkyl group or an aryl group which is optionally substituted; L' represents in particular an oxygen atom or a phenylamino group optionally substituted by one or more alkyl or M⁺(O)$_m$S(O⁻)— groups, with m and M⁺ as defined above;

Q and Q', which are identical or different, represent an oxygen or sulfur atom; in particular, Q and Q' represent an oxygen atom;

M⁺ is as defined above;

Mention may be made, as examples of dyes of formula (XV), of: Acid Yellow 73, Acid Red 51, Acid Red 52, Acid Red 87, Acid Red 92, Acid Red 95 and Acid Violet 9;

f) indole-based dyes of formula (XVI):

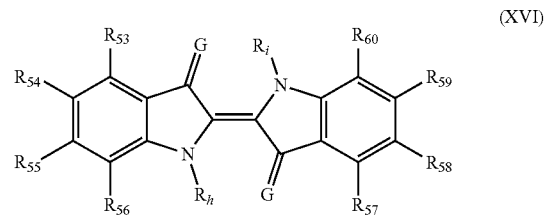

(XVI)

$R_{53}$, $R_{54}$, $R_{55}$, $R_{56}$, $R_{57}$, $R_{58}$, $R_{59}$ and $R_{60}$, which are identical or different, represent a hydrogen atom or a group chosen from:
alkyl;
alkoxy, alkylthio;
hydroxyl, mercapto;
nitro, nitroso;
R°—C(X)—X'—, R°—X'—C(X)— or R°—X'—C(X)—X"—, with R° representing a hydrogen atom or an alkyl or aryl group and X, X' and X", which are identical or different, representing an oxygen or sulfur atom or NR, with R representing a hydrogen atom or an alkyl group;
M⁺(O)₂S(O⁻)—, with M⁺ representing a hydrogen atom or a cationic counterion;
M⁺(O)CO⁻—, with M⁺ as defined above;
G represents an oxygen or sulfur atom or an NR$_e$ group, with R$_e$ as defined above; in particular, G represents an oxygen atom;
R$_i$ and R$_h$, which are identical or different, represent a hydrogen atom or an alkyl group;

it being understood that the formula (XVI) comprises at least one sulfonate radical M⁺(O)₂S(O⁻)— or one carboxylate radical M⁺C(O)O⁻—; preferentially sodium sulfonate;

Mention may be made, as examples of dyes of formula (XVI), of: Acid Blue 74.

g) quinoline-derived dyes of formula (XVII):

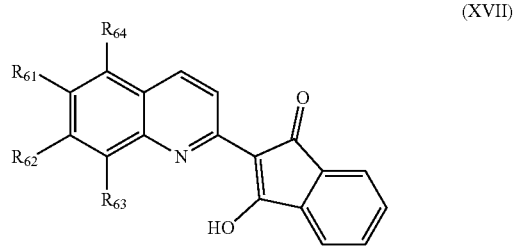

(XVII)

$R_{61}$ represents a hydrogen or halogen atom or an alkyl group;

$R_{62}$, $R_{63}$ and $R_{64}$, which are identical or different, represent a hydrogen atom or an M⁺(O)₂S(O⁻)— group, with M⁺ representing a hydrogen atom or a cationic counterion; or else $R_{61}$ with $R_{62}$ or $R_{61}$ with $R_{64}$ together form a benzo group optionally substituted by one or more M⁺(O)₂S(O⁻)— groups, with M⁺ representing a hydrogen atom or a cationic counterion;

it being understood that the formula (XVII) comprises at least one sulfonate radical $M^+(O)_2S(O^-)$—, preferentially sodium sulfonate;

Mention may be made, as examples of dyes of formula (XVII), of: Acid Yellow 2, Acid Yellow 3 and Acid Yellow 5.

Mention may be made, among the natural direct dyes which can be used according to the invention, of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts can also be used.

Preferably, the direct dyes are chosen from anionic direct dyes.

The coloring agent(s) can be present in a total amount ranging from 0.001% to 15% by weight, preferably from 0.005% to 10% by weight, with respect to the total weight of the composition.

The pigments can be present in a total amount ranging from 0.05% to 15% by weight, preferably from 0.1% to 10% by weight, with respect to the total weight of the composition.

The direct dye(s) can be present in a total amount ranging from 0.001% to 10% by weight of the total weight of the composition, preferably from 0.005% to 5% by weight of the total weight of the composition.

Preferably, the composition according to the invention comprises water. Preferably, the water is present in a content ranging from 0.1% to 50% by weight, more preferentially from 0.5% to 40% by weight, with respect to the total weight of the composition.

The composition can comprise less than 2% by weight of water, with respect to the total weight of the composition.

Organic Solvents:

The process according to the invention comprises a composition according to the invention which can comprise one or more organic solvents.

Mention may be made, as organic solvent, for example, of lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols, such as benzyl alcohol or phenoxyethanol, and their mixtures.

Preferably, the composition comprises one or more organic solvents chosen from lower $C_1$-$C_4$ alkanols, more preferentially ethanol.

The organic solvent(s) can be present in a total amount of inclusively between 0.5% and 80% by weight, with respect to the total weight of the composition, preferably between 1% and 70% by weight, more preferentially of inclusively between 5% and 60%, better still between 10% and 50% by weight, with respect to the total weight of the composition.

Additives:

The process according to the invention comprises a composition according to the invention which can contain any adjuvant or additive generally used.

Mention may be made, among the additives capable of being contained in the composition, of reducing agents, thickening agents, softeners, antifoaming agents, moisturizing agents, UV-screening agents, peptizers, solubilizers, fragrances, anionic, cationic, nonionic or amphoteric surfactants, proteins, vitamins, polymers, preservatives, waxes and their mixtures.

The composition according to the invention can be provided in particular in the form of a suspension, a dispersion, a gel, an emulsion, in particular an oil-in-water (O/W) or water-in-oil (W/O) emulsion, or a multiple (W/O/W or polyol/O/W or O/W/O) emulsion, in the form of a cream, a foam, a stick, a dispersion of vesicles, in particular of ionic or nonionic lipids, or a two-phase or multiphase lotion.

In a preferred embodiment, the composition according to the invention is an aqueous and/or aqueous-alcoholic system.

A person skilled in the art can select the appropriate formulation form, and also its method of preparation, on the basis of his or her general knowledge, taking into account first the nature of the constituents used, in particular their solubility in the support, and secondly the application envisaged for the composition.

According to a preferred embodiment, the composition according to the invention comprises 3-aminopropyltriethoxysilane (APTES), at least one nonamino silicone of formula (II) as described above and at least one pigment.

According to a more preferred embodiment, the composition according to the invention comprises 3-aminopropyltriethoxysilane (APTES), at least one nonamino silicone of formula (III) as described above and at least one pigment.

Process for the Treatment of Keratin Fibers

The present invention relates to a process for the treatment of keratin fibers, such as the hair, comprising the application, to the keratin fibers, of a composition as described above, followed by a stage of application of heat to the keratin fibers covered with the composition, using a heating tool, at a temperature of greater than or equal to 45° C. for a period of time of greater than or equal to 15 minutes.

Preferably, the composition according to the invention is a composition for dyeing keratin fibers, such as the hair.

The composition according to the invention can be used on wet or dry keratin fibers, and also on all types of fair or dark, natural or dyed, permanent-waved, bleached or relaxed, fibers.

According to a specific embodiment of the process of the invention, the fibers are washed before application of the composition described above.

The application of the dye composition to the keratin fibers can be carried out by any conventional means, in particular by means of a comb, a fine brush, a coarse brush or with the fingers.

The dyeing process, i.e. application of the dye composition to the keratin fibers, is generally carried out at ambient temperature (between 15° C. and 25° C.).

Preferably, after application of the composition according to the invention and before the stage of application of heat to the keratin fibers, the keratin fibers are subjected to a drying stage, for example, using a hairdryer, for a period of time of between 1 minute and 5 minutes.

Preferably, after application of the composition according to the invention to the keratin fibers, there is a waiting time of at least 30 seconds, preferably of at least 1 minute and more preferentially of at least 5 minutes, before the stage of drying the keratin fibers.

After application of the composition according to the invention and optionally a stage of drying the keratin fibers, the process according to the invention comprises a stage of application of heat to the keratin fibers, using a heating tool, at a temperature of greater than or equal to 45° C. for a period of time of greater than or equal to 15 minutes.

Preferably, the stage of application of heat to the keratin fibers, using a heating tool, is carried out at a temperature of greater than or equal to 45° C. for a period of time of greater than or equal to 30 minutes, more preferentially at a temperature of greater than or equal to 45° C. for a period of time of greater than or equal to 1 hour.

More preferentially still, the stage of application of heat to the keratin fibers, using a heating tool, is carried out at a temperature of greater than or equal to 60° C. for a period of time of greater than or equal to 15 minutes, better still at a temperature of greater than or equal to 60° C. for a period of time of greater than or equal to 30 minutes.

The stage of application of heat of the process of the invention can be carried out using a hood, a hairdryer, a straightening iron, a curling iron, a Climazon, and the like.

Preferably, the stage of application of heat of the process of the invention is carried out using a hairdryer.

Preferably, the heating tool is a hairdryer.

During the stage of application of heat to the keratin fibers, a mechanical action may be exerted on the locks, such as combing, brushing or running the fingers through.

In a specific alternative form, the process of the invention employs a stage (b1) of application of heat using a hood, a hairdryer or a Climazon, preferably a hairdryer, and a stage (b2) of application of heat using a straightening or curling iron, preferably a straightening iron.

Stage (b1) can be carried out before stage (b2).

During stage (b1), also known as drying stage, the fibers are dried at a temperature of greater than or equal to 45° C. for a period of time of greater than or equal to 15 minutes. According to a specific embodiment, this temperature is greater than or equal to 45° C. and less than 110° C.

Preferably, if the fibers are dried, they are dried, in addition to a supply of heat, with a flow of air. This flow of air during the drying makes it possible to improve the individualization of the sheathing.

During the drying, a mechanical action may be exerted on the locks, such as combing, brushing or running the fingers through.

During stage (b2), the passage of the straightening or curling iron, preferably the straightening iron, can be carried out at a temperature ranging from 110° C. to 220° C., preferably between 140° C. and 200° C.

Preferably, after application of the composition according to the invention to the keratin fibers and after the stage of application of heat to the keratin fibers, using a heating tool, there is a waiting time of at least 30 minutes before the first shampooing operation, preferably at least 1 h before the first shampooing operation, more preferentially at least 10 h before the first shampooing operation, better still at least 24 h before the first shampooing operation.

The present invention also relates to a process for the treatment of keratin fibers, such as the hair, which consists in extemporaneously mixing, at the time of use, two compositions (A) and (B) and in applying the mixture to the fibers, with:
the composition (A) comprising at least one alkoxysilane chosen from the compounds of formula (I) as described above, their oligomers and/or their mixtures;
the composition (B) comprising at least one nonamino silicone of formula (II) as described above;
it being understood that the composition (A) and/or the composition (B) comprise at least one coloring agent chosen from pigments, direct dyes and their mixtures;
followed by a stage of application of heat to the keratin fibers covered with the composition, using a heating tool, at a temperature of greater than or equal to 45° C. for a period of time of greater than or equal to 15 minutes.

Preferably, the composition (A) does not comprise at least one nonamino silicone of formula (II) and the composition (B) does not comprise at least one alkoxysilane chosen from the compounds of formula (I), their oligomers and/or their mixtures.

According to a first embodiment, the coloring agent is present in the composition (B). Thus, the composition (A) and the composition (B) are mixed extemporaneously at the time of use before being applied to the keratin fibers.

According to a second embodiment, the coloring agent is present in the composition (A). Thus, the composition (A) and the composition (B) are mixed extemporaneously at the time of use before being applied to the keratin fibers.

According to a third embodiment, the coloring agent is present in a composition (D). Thus, the composition (A), the composition (B) and the composition (D) are mixed extemporaneously at the time of use before being applied to the keratin fibers.

Preferably, the composition (B) comprises at least one coloring agent chosen from pigments, direct dyes and their mixtures.

The present invention will now be described more specifically by means of examples, which do not in any way limit the scope of the invention. However, the examples make it possible to support preferred embodiments, alternative forms and specific characteristics of the invention.

EXAMPLE

In the examples, the temperature is given in degrees Celsius and corresponds to ambient temperature (20-25° C.), unless otherwise indicated, and the pressure is atmospheric pressure, unless otherwise indicated.

The following compositions are prepared (in g/100 g, AM: Active material):

Composition 1 below (i.e. solution of 3-aminopropyltriethoxysilane (APTES)) is prepared according to the process below:

APTES (APTES Silsoft A-1100, sold by Momentive Performance Materials) is mixed with an water to form an aqueous solution then the pH is adjusted to 11 by addition of HCl solution having a pH=1, and said mixture is placed on a magnetic stirrer of the VWR brand (rotational speed 500 rpm) at ambient temperature for 24 hours. The pH of the mixture is equal to 11.

TABLE 1

| Composition | 1 |
|---|---|
| 3-Aminopropyltriethoxysilane (APTES) | 30 |
| Hydrochloric acid (HCl) | 0.02 |
| Water | q.s. for 100 |

Composition 2 below (i.e. alcoholic solution of silicone) is prepared according to the process below:
the non amino silicone compound is diluted in an ethanol solution in which the pigment (iron oxide sold by Sun Chemical under the name SunPuro Red Iron Oxide®) is dispersed.

TABLE 2

| Composition | 2 |
|---|---|
| Non amino silicone | 19.68 AM |
| Pigment (iron oxide sold by Sun | 5.72 |

TABLE 2-continued

| Composition | 2 |
|---|---|
| Chemical under the name SunPuro Red Iron Oxide ®) | |
| Ethanol | q.s. for 100 |

Composition 1 is mixed with composition 2 according to a 50:50 ratio. The following composition is prepared according to the above protocol:

TABLE 3

| Compositions | A (Invention) |
|---|---|
| Polydimethylsiloxane (PDMS) having hydroxyl end functional groups (481939, sold by Sigma-Aldrich) | 9.8 AM |
| Pigment | 2.9 |
| 3-Aminopropyltriethoxysilane | 15 |
| Hydrochloric acid (HCl) | 0.01 |
| Water | 35 |
| Denatured ethyl alcohol | q.s. for 100 |
| Molecular weight (in g/mol) | <1500 |

Protocol:

The composition A is applied to locks of dry natural hair having 90% white hairs, in a proportion of 1 g of composition per gram of lock.

The locks of hair are left at ambient temperature for 5 min.

The locks of hair are subsequently combed and dried with a hairdryer for 3 minutes.

The locks of hair are subsequently subjected to a stage of application of heat according to different temperature conditions and for a given time.

The locks of hair are placed in a temperature-controlled oven (Memmert oven).

The conditions evaluated are as follows:
temperature of 45° C. for 15 minutes,
temperature of 45° C. for 30 minutes,
temperature of 45° C. for 1 h and
temperature of 60° C. for 30 minutes.

After the passages in the oven, the locks of hair are left at ambient temperature for 24 h.

A comparative lock dyed with the composition A according to the invention and not subjected to a stage of application of heat is also prepared according to the protocol above. This lock of hair is left at ambient temperature for 24 h.

The locks of hair thus dyed and subjected or not subjected to a stage of application of heat are subsequently subjected to a test of several repeated shampooing operations so as to evaluate the fastness (the persistence) of the coloring obtained toward shampooing operations, according to the protocol of the shampooing operation described below.

Protocol of the Shampooing Operation:

The locks are washed using a standard shampoo (Garnier Ultra Doux).

The locks of hair are subsequently rinsed, combed and dried with a hairdryer.

The following shampooing operation is carried out on the locks obtained after the application of the hairdryer.

Results:

The persistence of the color of the locks was evaluated in the CIE L*a*b* system, using a Minolta Spectrophotometer CM3600A colorimeter (illuminant D65, angle 10°, specular component included).

In this L*a*b* system, L* represents the intensity of the color, a* indicates the green/red color axis and b* indicates the blue/yellow color axis.

The persistence of the coloring is evaluated by the color difference ΔE between the dyed locks before shampooing, then after having undergone five shampooing operations according to the protocol described above. The lower the ΔE value, the more persistent the color toward shampooing operations.

The ΔE value is calculated according to the following equation:

$$\Delta E = \sqrt{(L^* - L_0^*)^2 + (a^* - a_0^*)^2 + (b^* - b_0^*)^2}$$

In this equation, L*a*b* represent the values measured after dyeing the hair and after having undergone shampooing operations, and $L_0^*a_0^*b_0^*$ represent the values measured after dyeing the hair but before shampooing operations.

TABLE 4

| Compositions | Number of shampooing operations | L* | a* | b* | ΔE |
|---|---|---|---|---|---|
| Comparative lock | 0 | 39.62 | 32.92 | 27.30 | — |
| | 5 | 48.70 | 22.57 | 22.67 | 14.53 |
| Lock 1 (temperature of 45° C. for 15 minutes) | 0 | 39.62 | 32.92 | 27.30 | — |
| | 5 | 42.32 | 27.08 | 23.58 | 7.43 |
| Lock 2 (temperature of 45° C. for 30 minutes) | 0 | 39.62 | 32.92 | 27.30 | — |
| | 5 | 42.42 | 30.54 | 25.63 | 4.04 |
| Lock 3 (temperature of 45° C. for 1 h) | 0 | 39.62 | 32.92 | 27.30 | — |
| | 5 | 40.17 | 31.78 | 26.14 | 1.72 |
| Lock 4 (temperature of 60° C. for 30 minutes) | 0 | 39.50 | 32.39 | 27.17 | — |
| | 5 | 40.10 | 32.69 | 27.11 | 0.67 |

The locks of hair 1, 2, 3 and 4 dyed with the composition A according to the invention, subjected to a stage of application of heat and washed with five successive shampooing operations, exhibit low ΔE values, in comparison with the comparative lock of hair dyed with the composition A according to the invention, not subjected to a stage of application of heat and washed with five successive shampooing operations.

Thus, the colored coating of the keratin fibers which is obtained with the process according to the invention exhibits good resistance to shampooing. Indeed, the locks of hair dyed with the process according to the invention and washed with five shampooing operations exhibit good persistence of the color.

The invention claimed is:

1. A process for the treatment of keratin fibers, comprising:
applying to the keratin fibers a composition comprising:
a) at least one alkoxysilane chosen from the compounds of formula (I), oligomers thereof, or mixtures thereof:

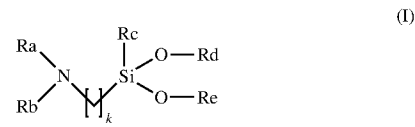

wherein:
Ra and Rb are independently chosen from a hydrogen atom; an alkyl group having from 1 to 20 carbon atoms; a cycloalkyl group having from 3 to 20 carbon atoms; an aryl group having from 6 to 12 carbon atoms; or an aminoalkyl group having from 1 to 20 carbon atoms;
Rc represents a hydrogen atom; an alkyl group having from 1 to 20 carbon atoms; an alkoxy group having from 1 to 10 carbon atoms;
Rd and Re are independently chosen from an alkyl group having from 1 to 10 carbon atoms; and
k denotes an integer ranging from 0 to 5;
b) at least one non amino silicone of formula (II):

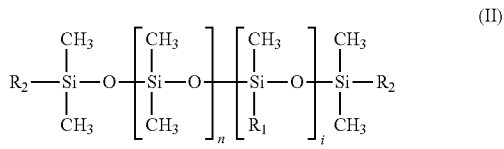
(II)

wherein:
$R_1$ is chosen from an alkyl group having from 1 to 10 carbon atoms, or an alkoxy group having from 1 to 2 carbon atoms or an $-O_x-(X)_p-Si(OR_3)_3$ group with X representing a saturated divalent hydrocarbon radical having 1 carbon atom, $R_3$ representing an alkyl group having from 1 to 4 carbon atoms, x denoting an integer equal to 0 or 1 and p denoting an integer ranging from 0 to 4;
$R_2$ is independently chosen from a hydroxyl group or an alkoxy group having from 1 to 2 carbon atoms;
i denotes an integer ranging from 0 to 18, n denotes an integer ranging from 0 to 18 with n+i ranging from 4 to 18,
the non-amino silicones of formula (II) having a weight-average molecular weight of less than or equal to 1500 g/mol; and
c) at least one coloring agent chosen from pigments, direct dyes, or mixtures thereof, applying heat to the keratin fibers covered with the composition, using a heating tool, at a temperature of greater than or equal to 45° C. for a period of time of greater than or equal to 15 minutes.

2. The process of claim 1, wherein in the at least one alkoxysilanes of formula (I),
Ra and Rb are independently chosen from a hydrogen atom; or Ra denotes a hydrogen atom and Rb denotes a cycloalkyl group having from 3 to 20 carbon atoms;
Rc represents an alkyl group having from 1 to 10 carbon atoms;
Rd and Re are independently chosen from an alkyl group having from 1 to 10 carbon atoms; and
k denotes an integer ranging from 1 to 3.

3. The process of claim 1, wherein in the at least one alkoxysilanes of formula (I):
Ra and Rb are independently chosen from a hydrogen atom;
Rc represents an alkoxy group having from 1 to 4 carbon atoms;
Rd and Re are independently chosen from an alkyl group having from 1 to 4 carbon atoms; and
k denotes an integer equal to 1 or 3.

4. The process of claim 1, wherein the at least one alkoxysilanes of formula (I) are chosen from 3-aminopropyltriethoxysilane (APTES), 3-aminopropylmethyldiethoxysilane (APMDES), N-cyclohexylaminomethyltriethoxysilane, or mixtures thereof.

5. The process of claim 1, wherein the alkoxysilanes of formula (I) are present in a total amount ranging from 0.1% to 30% by weight, with respect to the total weight of the composition.

6. The process of claim 1, wherein in the at least one non-amino silicones of formula (II),
$R_1$ independently represents an alkyl group having from 1 to 10 carbon atoms;
$R_2$ independently represents a hydroxyl group or an alkoxy group having from 1 to 2 carbon atoms; and
i denotes an integer ranging from 0 to 18, n denotes an integer ranging from 0 to 18 with n+i varying from 4 to 18.

7. The process of claim 1, wherein in the at least one non-amino silicones of formula (II),
$R_1$ independently represents an alkyl group having from 1 to 4 carbon atoms;
$R_2$ independently represents a hydroxyl group; and
i denotes an integer ranging from 0 to 18, n denotes an integer ranging from 0 to 18 with n+i varying from 4 to 18.

8. The process of claim 1, wherein the at least one non-amino silicones of formula (II) have an average molecular weight ranging from 460 g/mol to 1500 g/mol.

9. The process of claim 1, wherein the non-amino silicones of formula (II) are present in a total amount ranging from 0.1% to 30% by weight, with respect to the total weight of the composition.

10. The process of claim 1, wherein the weight ratio of alkoxysilanes of formula (I) to non-amino silicones of formula (II) ranges from 95:5 to 5:95.

11. The process of claim 1, further comprising water present in an amount ranging from 0.1% to 50% by weight, with respect to the total weight of the composition.

12. The process of claim 1, wherein:
the coloring agents are present in a total amount ranging from 0.001% to 15%, with respect to the total weight of the composition; and,
the coloring agents are chosen from pigments.

13. The process of claim 1, wherein the application of heat to the keratin fibers, using a heating tool, is carried out at a temperature of greater than or equal to 45° C. for a period of time of greater than or equal to 30 minutes.

14. The process of claim 1, wherein the application of heat to the keratin fibers, using a heating tool, is carried out at a temperature of greater than or equal to 60° C. for a period of time of greater than or equal to 15 minutes.

15. A process for treating keratin fibers, comprising:
extemporaneously mixing, at the time of use, composition (A) and composition (B) and applying the mixture to the fibers, wherein:
composition (A) comprises at least one alkoxysilane chosen from the compounds of formula (I), their oligomers thereof, or mixtures thereof:

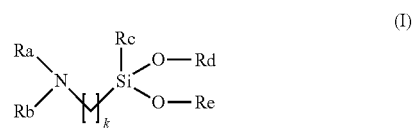
(I)

wherein:
Ra and Rb are independently chosen from a hydrogen atom; an alkyl group having from 1 to 20 carbon atoms; a cycloalkyl group having from 3 to 20 carbon atoms; an aryl group having from 6 to 12 carbon atoms; or an aminoalkyl group having from 1 to 20 carbon atoms;
Rc represents a hydrogen atom; an alkyl group having from 1 to 20 carbon atoms; an alkoxy group having from 1 to 10 carbon atoms;
Rd and Re are independently chosen from an alkyl group having from 1 to 10 carbon atoms; and
k denotes an integer ranging from 0 to 5;
composition (B) comprises at least one non-amino silicone of formula (II):

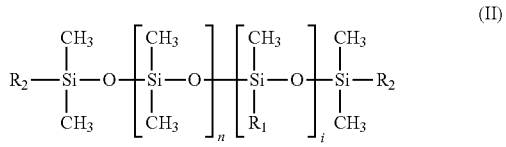

wherein:
$R_1$ is chosen from an alkyl group having from 1 to 10 carbon atoms, or an alkoxy group having from 1 to 2 carbon atoms or an $-O_x-(X)_p-Si(OR_3)_3$ group with X representing a saturated divalent hydrocarbon radical having 1 carbon atom, $R_3$ representing an alkyl group having from 1 to 4 carbon atoms, x denoting an integer equal to 0 or 1 and p denoting an integer ranging from 0 to 4;
$R_2$ is independently chosen from a hydroxyl group or an alkoxy group having from 1 to 2 carbon atoms;
i denotes an integer ranging from 0 to 18, n denotes an integer ranging from 0 to 18 with n+i ranging from 4 to 18,
the non-amino silicone(s) of formula (II) having a weight-average molecular weight of less than or equal to 1500 g/mol; and
at least one of composition (A) or composition (B) comprises at least one coloring agent chosen from pigments, direct dyes and their mixtures; and
applying heat to the keratin fibers covered with the mixture, using a heating tool, at a temperature of greater than or equal to 45° C. for a period of time of greater than or equal to 15 minutes.

16. The process of claim 15, wherein the alkoxysilane(s) of formula (I) are present in a total amount ranging from 0.1% to 30% by weight, with respect to the total weight of composition (A) and composition (B).

17. The process of claim 15, wherein the at least one non-amino silicones of formula (II) have an average molecular weight ranging from 460 to 1500 g/mol.

18. The process of claim 15, wherein the non-amino silicones of formula (II) are present in a total amount ranging from 0.1% to 30% by weight, with respect to the total weight of composition (A) and composition (B).

19. The process of claim 15, wherein the weight ratio of alkoxysilane(s) of formula (I) to non-amino silicones of formula (II) ranges from 95:5 to 5:95.

20. The process of claim 15, further comprising water in amount ranging from 0.1% to 50% by weight, with respect to the total weight of the mixture.

* * * * *